United States Patent [19]

Savic et al.

[11] 4,140,109
[45] Feb. 20, 1979

[54] IMPEDANCE-BASED METHOD AND APPARATUS FOR MONITORING CRYODESTRUCTION IN CONTROLLED CRYOSURGERY

[76] Inventors: Michael I. Savic, 4 Saw Mill Dr., Wilbraham, Mass. 01095; Setrag A. Zacarian, 154 Colony Rd., Longmeadow, Mass. 01106

[21] Appl. No.: 842,733

[22] Filed: Oct. 17, 1977

[51] Int. Cl.² ............................................. A61B 5/00
[52] U.S. Cl. ................................. 128/2.1 Z; 128/2 H; 128/303.1; 128/399
[58] Field of Search ............... 128/2 H, 2.1 R, 2.1 Z, 128/303 R, 303.1, 399

[56] References Cited

U.S. PATENT DOCUMENTS

| | | | |
|---|---|---|---|
| 3,651,694 | 3/1972 | Lamb | 128/2 H |
| 3,948,269 | 4/1976 | Zimmer | 128/303.1 |
| 3,980,073 | 9/1976 | Shaw | 128/2.1 Z |
| 4,016,886 | 4/1977 | Doss et al. | 128/399 |

*Primary Examiner*—William E. Kamm
*Attorney, Agent, or Firm*—Ross, Ross & Flavin

[57] ABSTRACT

An impedance-based method for the controlled cryosurgery of a patient's malignant tumor consisting of the steps: placing a contact electrode electrically connected to an impedance meter in electric contact with a body site spaced away from the tumor target, inserting a needle electrode electrically connected to the impedance meter through the tumor target with the tip of the needle electrode penetrating the immediately underlying normal tissue therebelow, and monitoring during cryosurgery the impedance between the two electrodes as a reflection of the eutectic state of the tissue circumadjacent the tip of the needle electrode.

13 Claims, 4 Drawing Figures

IMPEDANCE-BASED METHOD AND APPARATUS FOR MONITORING CRYODESTRUCTION IN CONTROLLED CRYOSURGERY

This invention relates to cryogenic techniques in medical and surgical practice involving the monitoring of cryodestructive temperatures by means of measuring the electrical characteristic of impedance in the case of biological tissue of either humans or animals.

The desideratum in controlled cryonecrosis is to destroy the abnormal tissue while yet preserving the healthy tissue surrounding the area of the tumoral target.

One of the major problems in destructive cryosurgery is to know the exact temperature of the tissue targeted to obtain cryonecrosis in the preselected area. The risks of either insufficient or excessive freezing are obviously to be avoided.

Freezing in cryosurgery ensues rapidly, surface cells being almost instantly frozen and brought to temperatures approximately that of liquid nitrogen, ($-196°$ C.), deeper layers of cells reaching freezing temperatures within a different time interval, they experiencing the extremely low temperatures of the surface. The formed extracellular ice causes the withdrawal of water across the cell membrane contributing to cell dehydration, a phenomenon which permits a marked increase of electrolytes within the cell leading to final shrinkage and collapse of its vital cell membrane, events incompatible with cell life.

It is safe to freeze tissue to at least $-20°$ C. in order to achieve a total phase change, that is, convert most of the available water to ice. The temperature generally accepted to be effective for lethal freezing of neoplasm is in the area of $-30°$ C. Only then can one be certain that the hypothermia will be effectual and lethal.

The eutectic temperature or lowest temperature at which a solution remains in a liquid state in the case of a solution of $KNO_3$, for instance, is $-2.9°$ C. That for a solution of NaCl is $-21.8°$ C. That for a solution of $CaCl_2$ is $-43.9°$ C. Such differing eutectic temperatures offer a most meaningful datum inasmuch as tissues and organs have a varied mixture and content of electrolytes so that therefore their eutectic zones vary considerably.

The pioneering work in this area by Dr. Patrick J. LePivert and associates of Saint-Etienne, France, involved thermal measurements monitoring the impedance between a pair of needles inserted on opposing margins of the neoplasm, with the freezing program ensuing until a temperature for complete intra and extracellular crystalization is reached.

It has been known by cryobiologists for many years that, with decreasing temperatures in tissue by means of freezing, one observes the increase of impedance within that tissue. LePivert made use of that principle by using one or more pairs of electrode needles for measuring impedance by low frequency. When the impedance reaches around 10 million ohms, the volume of tissue between electrodes is assumed to be at a cryodestructive temperature.

The inventors hereof determined that in using LePivert's technique, the prediction of cryodestructive temperatures at a certain depth in the tissue is definitely not accurate due to the very nature of LePivert's approach. "A New Impedance Based Method for Controlled Cryosurgery of Malignant Tumors" by Michael I. Savic, Eng.Sc.D., and Setrag A. Zacarian, M.D.,F.A.C.P.; The Journal of Dermatologic Surgery and Oncology, Vol. 3, No. 5, Nov.-Dec. 1977.

The measured impedance does not accurately reflect the temperature of the volume of tissue between the needle electrodes. In reality, it reflects the temperature around the inserted needles. As a consequence, when and if the entire tissue around each needle electrode is frozen below crystalization temperature except a small segment of each needle, i.e. its tip or point, the measured impedance represents approximately the impedance of the unfrozen tissue between these two segments, and the measured impedance will therefore not reflect cryodestruction of unwanted tissue, even if cryodestruction occurs. Contrariwise, if the entire tissue around either or both needles is frozen below crystalization temperature, the resultant impedance measurement indicates cryodestruction, even if the tumor between the two needles remains unfrozen; this for the reason that the tissue at such a temperature acts as an insulator and retards the current flow. Consequently, LePivert's technique does not work in either case.

The present invention is a reliable tool for monitoring cryodestructive temperatures at a specific depth in the tissue. The flow of current is such that the measuring current flows through the frozen tissue and therefore the measured impedance reflects the temperature of the frozen tissue.

The present invention commences with the basis premise that, with the employment of a single electrode needle and a distant contact electrode, the thermal history of the tissue circumadjacent the needle tip can be monitored, and comprehends the insertion of a primary electrode needle through the center of a tumor, or in the case of a larger tumor, the insertion of more than one such needle through critical sites thereof, each to a specified depth according to a reading of a calibration on the exterior needle wall so as to give an accurate measurement of the ice front and total cryolesion. A secondary contact electrode distantly of the primary electrode or electrodes allows the completion of the circuit and the measurement of the impedance between the electrodes. Monitoring the temperature at the measured depth or depths through a measuring of the impedance insures a total cryodestruction of the malignant cells.

This is all to say that the flow of current is such that the high impedance measured between the electrodes reflects the cryodestructive (Eutectic) temperatures of the tissue adjacent to the tip of the primary needle electrode.

Preferred embodiments of the invention have been set forth in detail in conjunction with the accompanying drawings wherein.

Figure 1:
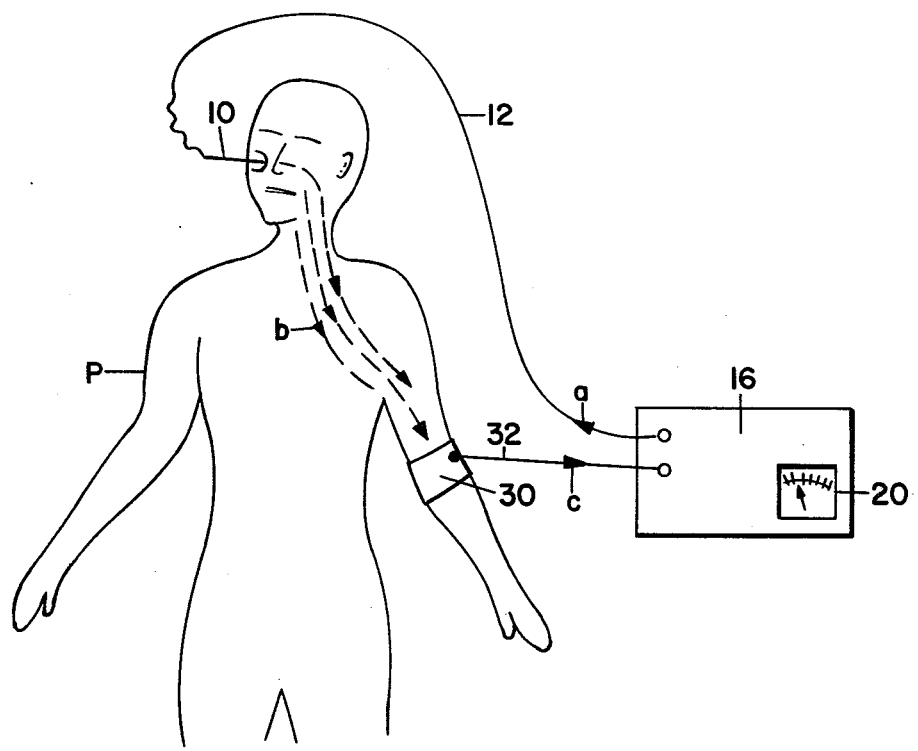
FIG. 1 is a diagrammatic representation of the invention as practiced upon a patient.

In accordance with the teaching hereof, an electrically uninsulated needle electrode 10, or insulated needle electrode with an uninsulated segment (normally the tip), which serves as a primary electrode and may be inserted perpendicularly or at various angles through the unwanted tumor of a patient P to a depth best estimated to be below the tumor depth. Primary electrode 10 is connected by a lead 12 to an impedance meter 16 provided with its own voltage source (not shown) and meter 20.

A patient contact or secondary electrode 30 is placed on the patient's body, distantly of the tumor, preferentially around his wrist in the manner of a wristlet, as one would execute in electrocardiography. The secondary electrode defines a conductive handcuff and serves the desideratum of providing a sufficiently large electrode surface for ensuring an optimum electrical contact. Such secondary electrode is connected by a lead 32 to impedance meter 16.

Current flow is as indicated by arrows a, b and c, being from impedance meter 16 to primary electrode 10 and thence through the body to secondary electrode 30 returnably to the impedance meter.

Figure 2:
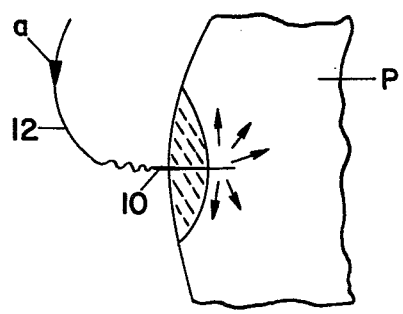
FIG. 2 is a fragmentary graphic representation in section showing the skin of a patient with a primary electrode extended through a tumor and showing the flow of the electric current from the needle tip.

As dramatized in FIG. 2, the current flows outwardly from the tip of primary electrode 10 inwardly of and slightly below the tumor site, the area desirably to be frozen.

Operationally, the cancer is frozen with a direct spray of liquid nitrogen applied at the target surface, wherefore crystalization ensues and penetrates inwardly of the tissue, the temperatures of the tissue layers closest to the surface being lowest; deeper within the tissue layers, the temperatures thereof being considerably higher. Tissue resistance increases with decreasing temperature so that the layers of tissue closer to the surface with the lower temperatures experience a higher resistance than do the deeper layers.

As crystalization reaches the area adjacent the innermost point or tip of the primary electrode, the measuring current drops significantly, thereby electrically insulating the needle from the rest of the body and establishing a correlation between the measured impedance and the cryodestructive temperature of the circumadjacent tissue around the electrode point.

Preferentially, the wall of the primary electrode is calibrated in millimeters to allow its insertion inwardly of the patient's skin surface to a predetermined depth and accordingly to ensure detection of the arrival of the cryodestructive temperature at the desired depth.

The impedance measurement between the electrodes gives essentially the impedance of the frozen tissue per se, the dominant impedance in the circuitry, the electrical parameters of human tissue being such that the impedance of the frozen tissue is much greater than the impedance of the measuring circuit itself, or the impedance between the primary electrode and the patient's tissue, or the impedance of the patient's body between the primary and secondary electrodes.

Experimentation has proven the excellence of the correlation between the measured impedance and temperature at a specific depth. Illustratively, with a temperature of approximately $-55°$ C. being registered at the tip of the primary electrode, the measured impedance was 2 M Ohms, establishing the possibility of predicting the cryodestructive temperature of the tissue around the point of the primary electrode by the monitoring of the impedance.

We have further observed, under our operating conditions, a correlation between the attainment of $-50°$ to $-60°$ C. in the cryolesion, within the tumor, and 2 million ohms recorded on the impedance meter, the $-50°$ to $-60°$ C. temperature range thus being recommended as the most lethal for effective cryonecrosis of malignant neoplasia.

Figure 3:
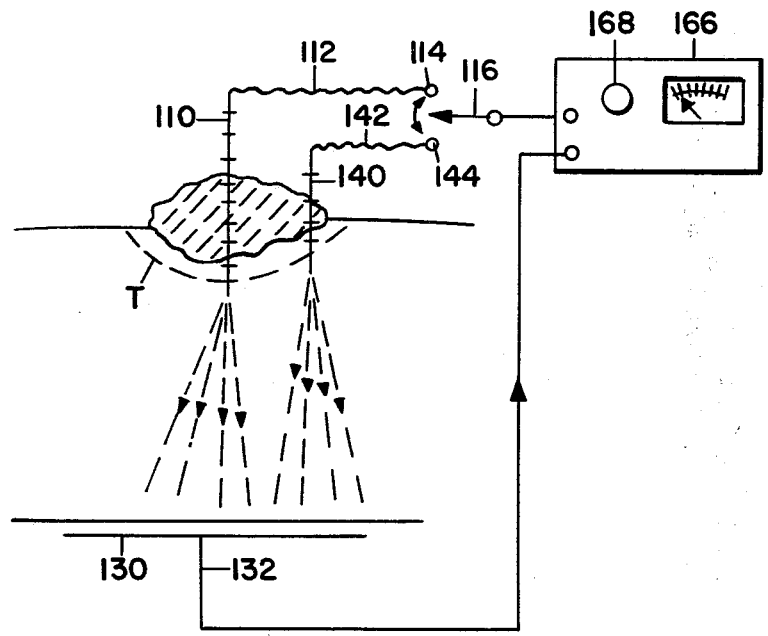
FIG. 3 is a schematic diagram of the circuit of the invention when more than one primary needle is employed, one centrally of and one at another site in the tumor.

Using more than one needle, as shown in FIG. 3, the cryodestructive temperature in other critical points can be monitored. This would be for the purpose of measuring impedance at a point away from the center of the tumor target, say at one side or margin thereof so as to allow an independent measurement and insure against ineffective freezing and resultant recurrences.

A first primary electrode 110 is inserted through and centrally of the tumor T and is connected by the usual lead 112 to a terminal 114 of a switch 116.

A second primary electrode 140 is inserted at another site at or near one side of the tumor and is connected by a lead 142 to another terminal 144 of switch 116. The switch is connected to the impedance meter 166 by lead 168.

The secondary electrode 130 is connected by lead 132 to the impedance meter.

By the throw of switch 116, to alternate positions between primary electrodes 110 and 140, it is possible to selectively measure the impedance between each needle and the secondary electrode to selectively monitor cryodestructive temperature at more than one critical point.

If desired, a signal 168 of auditory or visual type may be provided in the impedance meter and may be preset so as to signal when a predetermined impedance value shall have been reached.

If desired, more than two such needles, say three or four or five, may be employed for the monitoring of the temperature at more than two such critical sites.

The salient point is that the correlation is established between the measured impedance and the cryodestructive temperature of the tissue around the point of each needle. As each needle is calibrated, it is thus possible to detect when the cryodestructive temperature reaches the desired depth.

Figure 4:
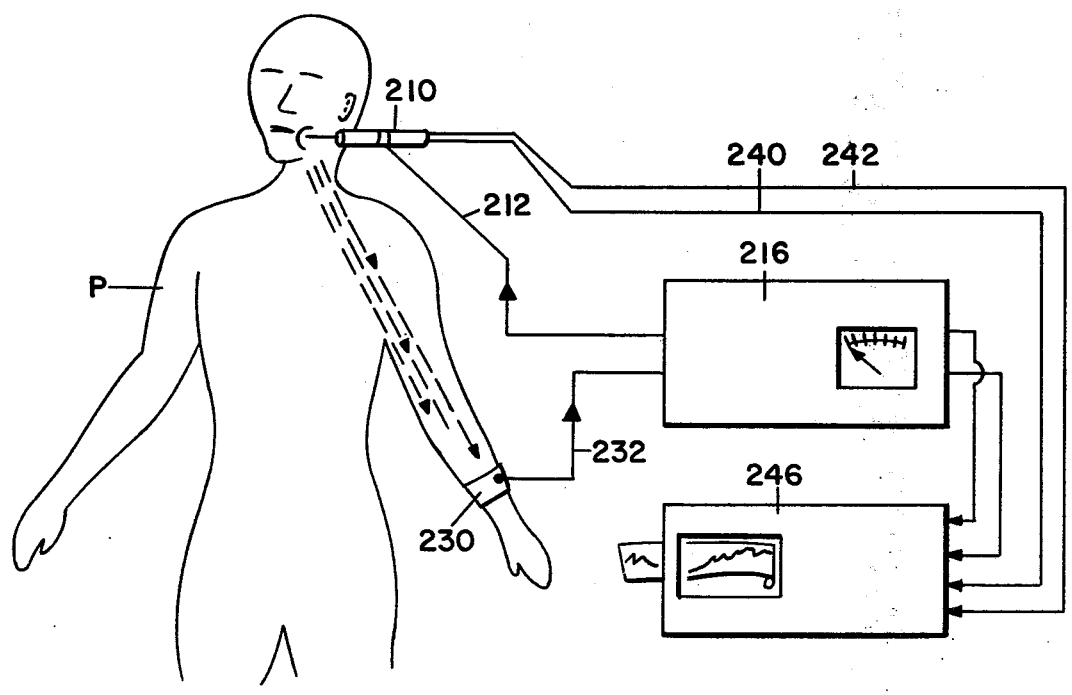
FIG. 4 is another diagrammatic representation of monitoring being practiced as recordation ensues.

In actual practice, using an arrangement such as illustrated in FIG. 4, it is possible to record the correlation between temperature and impedance. A thermocouple needle 210 is used at the situs of the patient's tumor, the needle serving not only as a primary electrode for the measurement of the impedance through lead 212 to impedance meter 216 but also as a thermocouple needle for the measurement of the temperature through leads 240 and 242 to a recorder 246.

The secondary electrode 230, as in the FIG. 1 exemplification, is placed around the patient's body, as at the wrist, and is connected by a lead 232 to impedance meter 216.

In the freezing of a given tumor target, the impedance increases proportionately with the lowering of the temperature and under an established set of conditions at a range between $-50°$ C. to $-60°$ C., the impedance consistently registers at 2 megohms. This range of impedance reflects the total crystallization of electrolytes and the congelation of cells. At these temperatures, all existing solution within the cell is in solid state and the hydrogen ion concentration within the cell is so great that it is no longer compatible with life.

We claim:

1. An impedance-based method for the controlled cryosurgery of a patient's malignant tumor consisting of the steps: placing a contact electrode electrically connected to an impedance meter in electric contact with a body site spaced away from the tumor target, inserting a needle electrode electrically connected to the impedance meter through the tumor target with the tip of the needle electrode penetrating the immediately underlying normal tissue therebelow, and monitoring during cryosurgery the impedance between the two electrodes as a reflection of the eutectic state of the tissue circumadjacent the tip of the needle electrode.

2. The method as set forth in claim 1, with the dominant impedance within the circuit being the impedance between the needle electrode tip and circumadjacent tissue.

3. The method as set forth in claim 1, with the impedance between the needle electrode tip and circumadjacent tissue being the dominant impedance among the plurality of impedances connected in series in the circuitry.

4. In the method as set forth in claim 1, the monitoring being conducted in seriatim at a plurality of selected sites of the tumor target.

5. In the method as set forth in claim 1, including the step of terminating the lethal freezing of the neoplasm at its eutectic state as indicated by a visual signal generated upon attainment of a high value of the impedance.

6. In the method as set forth in claim 1, including the step of terminating the cryodestructive procedure at the critical end point as indicated by an auditory signal generated upon attainment of a high value of the impedance.

7. In the method as set forth in claim 1 including the step of determining the depth of insertion of the needle electrode and depth of cryodestruction as reflected by the calibrations on the needle electrode.

8. Apparatus for monitoring the moment when a patient's malignant tumor reaches the eutectic state comprising in an electrical circuit: an impedance meter, a needle electrode electrically connected to the impedance meter, and a contact electrode electrically connected to the impedance meter, with the impedance meter indicating a measurement of the impedance between the electrodes as a reflection of the cryodestructive condition of the frozen tissue circumadjacent the needle electrode tip upon insertion through the tumor and into the underlying normal marginal tissue therebelow and with the contact electrode being in electric contact with a body site spaced away from the tumor.

9. In the apparatus as set forth in claim 8, including auditory signal means for generating an auditory signal by the attainment of a high value of the impedance.

10. In the apparatus as set forth in claim 8, including visual signal means for generating a visual signal by the attainment of a high value of the impedance.

11. In the apparatus as set forth in claim 8, including calibrations on the needle electrode for determining the depth of insertion of the needle electrode and accordingly the depth of the destruction by reading the calibrations on the needle electrode.

12. Apparatus for monitoring the moment when a patient's malignant tumor reaches the eutectic state cmprising in an electrical circuit: a plurality of needle electrodes for insertion into and through different sites in the target area, a contact electrode for placement in electrical contact with a body site outside of the target area, an impedance meter for measuring the impedance between the needle electrodes and contact electrode as a reflection of the cryodestructive condition of the frozen tissue circumadjacent each of the needle electrode tips, circuitry between the needle electrodes and contact electrode and impedance meter, and a switch for alternately and selectively connecting one of the needle electrodes of the plurality thereof to the impedance meter.

13. Apparatus for monitoring and recording the monitoring of the correlation between the temperature of the tissue circumadjacent the tip of a needle electrode inserted into and through a malignant tumor and the impedance between the needle electrode tip and circumadjacent tissue comprising: an impedance meter, a thermocouple needle electrode for insertion into and through the target area and being electrically connected to the impedance meter, a contact electrode for contacting with the patient's body at a point away from the target area and being electrically connected to the impedance meter, and a recorder for recording the measured temperature at the target area and the simultaneously measured impedance at the target area.

* * * * *